United States Patent
Perkins et al.

(10) Patent No.: US 10,302,809 B2
(45) Date of Patent: May 28, 2019

(54) BAND-LIMITED INTEGRATED COMPUTATIONAL ELEMENTS BASED ON HOLLOW-CORE FIBER

(71) Applicant: Halliburton Energy Services, Inc., Houston, TX (US)

(72) Inventors: David L. Perkins, The Woodlands, TX (US); Robert Atkinson, Conroe, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 66 days.

(21) Appl. No.: 15/306,017

(22) PCT Filed: May 21, 2015

(86) PCT No.: PCT/US2015/032063
§ 371 (c)(1),
(2) Date: Oct. 21, 2016

(87) PCT Pub. No.: WO2015/179703
PCT Pub. Date: Nov. 26, 2015

(65) Prior Publication Data
US 2017/0059740 A1 Mar. 2, 2017

Related U.S. Application Data

(60) Provisional application No. 62/002,579, filed on May 23, 2014.

(51) Int. Cl.
*G01J 3/00* (2006.01)
*G01V 8/16* (2006.01)
(Continued)

(52) U.S. Cl.
CPC ............... *G01V 8/16* (2013.01); *E21B 49/08* (2013.01); *G01N 9/00* (2013.01); *G01N 11/00* (2013.01);
(Continued)

(58) Field of Classification Search
CPC . G01V 8/16; E21B 49/08; G01N 9/00; G01N 11/00; G01N 21/31; G01N 33/2835
See application file for complete search history.

(56) References Cited

U.S. PATENT DOCUMENTS 6,385,380 B1 * 5/2002 Friedrich ........... G01N 21/6428
356/432
6,437,326 B1 8/2002 Yamate et al.
(Continued)

FOREIGN PATENT DOCUMENTS

JP 2012237684 A 12/2012
JP 2012242311 A 12/2012
(Continued)

*Primary Examiner* — Christine S. Kim
(74) *Attorney, Agent, or Firm* — Benjamin Fite; Parker Justiss, P.C.

(57) ABSTRACT

An optical analysis tool includes an integrated computational element (ICE). The ICE includes a first hollow-core fiber. The first hollow-core fiber has a structure configured such that a spectrum of light guided by the first hollow-core fiber is related, over a wavelength range, to a characteristic of the sample.

23 Claims, 7 Drawing Sheets

(51) Int. Cl.
  *G01N 9/00* (2006.01)
  *G01N 11/00* (2006.01)
  *G01N 21/31* (2006.01)
  *G01N 33/28* (2006.01)
  *E21B 49/08* (2006.01)
  *G01N 21/35* (2014.01)

(52) U.S. Cl.
  CPC ......... *G01N 21/31* (2013.01); *G01N 33/2835* (2013.01); *E21B 2049/085* (2013.01); *G01J 3/00* (2013.01); *G01N 21/35* (2013.01); *G01N 2021/3188* (2013.01); *G01N 2201/08* (2013.01); *G01N 2201/12* (2013.01)

(56) References Cited

U.S. PATENT DOCUMENTS

| | | | |
|---|---|---|---|
| 6,531,694 B2 | 3/2003 | Tubel et al. | |
| 7,595,882 B1* | 9/2009 | Chen | G01N 21/0303 356/301 |
| 7,657,141 B2* | 2/2010 | Imamura | G02B 6/02328 385/123 |
| 7,826,947 B2 | 11/2010 | Shal et al. | |
| 2005/0008291 A1* | 1/2005 | Baney | G01J 3/02 385/31 |
| 2006/0083470 A1* | 4/2006 | Solarz | G01N 21/8806 385/125 |
| 2007/0047598 A1* | 3/2007 | Liu | H01S 3/0064 372/6 |
| 2007/0274623 A1* | 11/2007 | Terrel | G02F 1/0136 385/11 |
| 2009/0066959 A1 | 3/2009 | Difoggio | |
| 2009/0323732 A1* | 12/2009 | Benabid | H01S 3/305 372/3 |
| 2010/0044103 A1* | 2/2010 | Moxley | E21B 7/14 175/16 |
| 2010/0220332 A1* | 9/2010 | Digonnet | G01C 19/722 356/465 |
| 2011/0059462 A1 | 3/2011 | Lim et al. | |
| 2012/0082410 A1* | 4/2012 | Peng | G02B 6/02304 385/11 |
| 2013/0022060 A1* | 1/2013 | Gaborel | G02B 6/4206 372/6 |
| 2015/0093085 A1* | 4/2015 | Byren | G02B 6/02314 385/125 |
| 2017/0045682 A1* | 2/2017 | Hoppe | G02B 6/02328 |

FOREIGN PATENT DOCUMENTS

| | | |
|---|---|---|
| WO | 2014042642 A1 | 3/2014 |
| WO | 2015179703 A1 | 11/2015 |

* cited by examiner

BAND-LIMITED INTEGRATED COMPUTATIONAL ELEMENTS BASED ON HOLLOW-CORE FIBER

CROSS-REFERENCE TO RELATED APPLICATION

This application is the National Stage of, and therefore claims the benefit of, International Application No. PCT/US2015/032063 filed on May 21, 2015, entitled "BAND-LIMITED INTEGRATED COMPUTATIONAL ELEMENTS BASED ON HOLLOW-CORE FIBER," which was published in English under International Publication Number WO 2015/179703 on Nov. 26, 2015, and has a priority date of May 23, 2014, based on application 62/002,579. Both of the above applications are commonly assigned with this National Stage application and are incorporated herein by reference in their entirety.

TECHNICAL FIELD

The subject matter of this disclosure is generally related to optical analysis systems for analyzing a substance of interest, for example, crude petroleum, gas, water, or other wellbore fluids. For instance, the disclosed optical analysis systems use a band-limited integrated computational element (ICE) that includes an ICE core monolithically coupled to one or more band-limiting filters, such that the either the ICE core, or the band-limiting filters, or both include hollow-core fiber.

BACKGROUND

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

ICEs enable the measurement of various chemical or physical characteristics through the use of regression techniques. An ICE selectively weights, when operated as part of optical analysis tools, light modified by a sample in at least a portion of a wavelength range such that the weightings are related to one or more characteristics of the sample. An ICE core can be an optical substrate with multiple stacked dielectric layers (e.g., from about 2 to about 50 layers), each having a different complex refractive index from its adjacent layers. The specific number of layers, N, the optical properties (e.g. real and imaginary components of complex indices of refraction) of the layers, the optical properties of the substrate, and the physical thickness of each of the layers that compose the ICE are selected so that the light processed by the ICE is related to one or more characteristics of the sample. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore gases and liquids, for instance.

DESCRIPTION OF DRAWINGS

Like reference symbols in the various drawings indicate like elements.

DETAILED DESCRIPTION

In accordance with the disclosed technologies, optical analysis systems use a band-limited ICE that includes an ICE core formed from a first hollow-core fiber and one or more band-limiting filters (e.g., an optical band-pass filter, etc.) formed from a second hollow-core fiber. Here, light guided through the ICE core formed from the first hollow-core fiber is modified by a sample, such that the sample modified light is related, over a wavelength range $[\lambda_{min}, \lambda_{max}]$, to a characteristic of the sample. Additionally, a band-limiting filter that is optically coupled to the ICE core and is formed from the second hollow-core fiber blocks guided light at wavelengths that are either shorter than $\lambda_{min}$ or longer than $\lambda_{max}$, or both. In this manner, the band-limiting filter formed from the second hollow-core fiber limits the sample modified light to the wavelength range $[\lambda_{min}, \lambda_{max}]$.

In accordance with the disclosed technologies, the hollow-core fibers can be engineered to impart an optical attenuation profile, similar to that provided by thin-film interference filters. The latter filters represent the basis of conventional band-limited ICE implementations for both the ICE core and optical band-pass filters. The hollow-core fibers also extend the optical wavelength range $[\lambda_{min}, \lambda_{max}]$ of the disclosed ICEs to the mid-infrared (mid-IR), which is currently a challenge for thin-film interference based ICE cores. In addition, the hollow-core fibers can be engineered to allow samples in the form of a gas to be channeled in the hollow cores for measuring properties of the gas.

Hollow-core fibers can be engineered with various lengths, varying number of main cores and auxiliary cores with various sizes, enabling the design of a complex structure and shape that would have similar optical transmission functions to that of band-limited ICEs. With this type of core structure, light from a light source can be introduced at one end of a hollow-core fiber cable. The light guided through such cable emerges at the opposing end thereof with an ICE-like optical spectrum. This represents the basis of a hollow-core fiber ICE.

In conventional ICE-based optical analysis tools, a small, built-in light source is dedicated to and typically built into the optical analysis tool. The use of hollow-core fiber based ICEs allows the light source to be remote from the measurement point. This may be useful at measurement points that are inaccessible to conventional ICE-based optical analysis tools. Further, the use of hollow-core fiber optic cable makes it possible to use a single light source for different optical analysis tools. Further, a single light source can be used in an optical analysis tool equipped with a hollow-core fiber based ICE to perform multiple analyte measurements. For example, several differently engineered hollow-core fibers can be bundled together in conjunction with a single broadband light source, allowing multiple analytes to be measured simultaneously.

Prior to describing example implementations of band-limited ICEs formed from hollow-core fibers, optical analysis tools based on the disclosed ICEs are described below along with examples of their use in oil/gas exploration.

Figure 1:
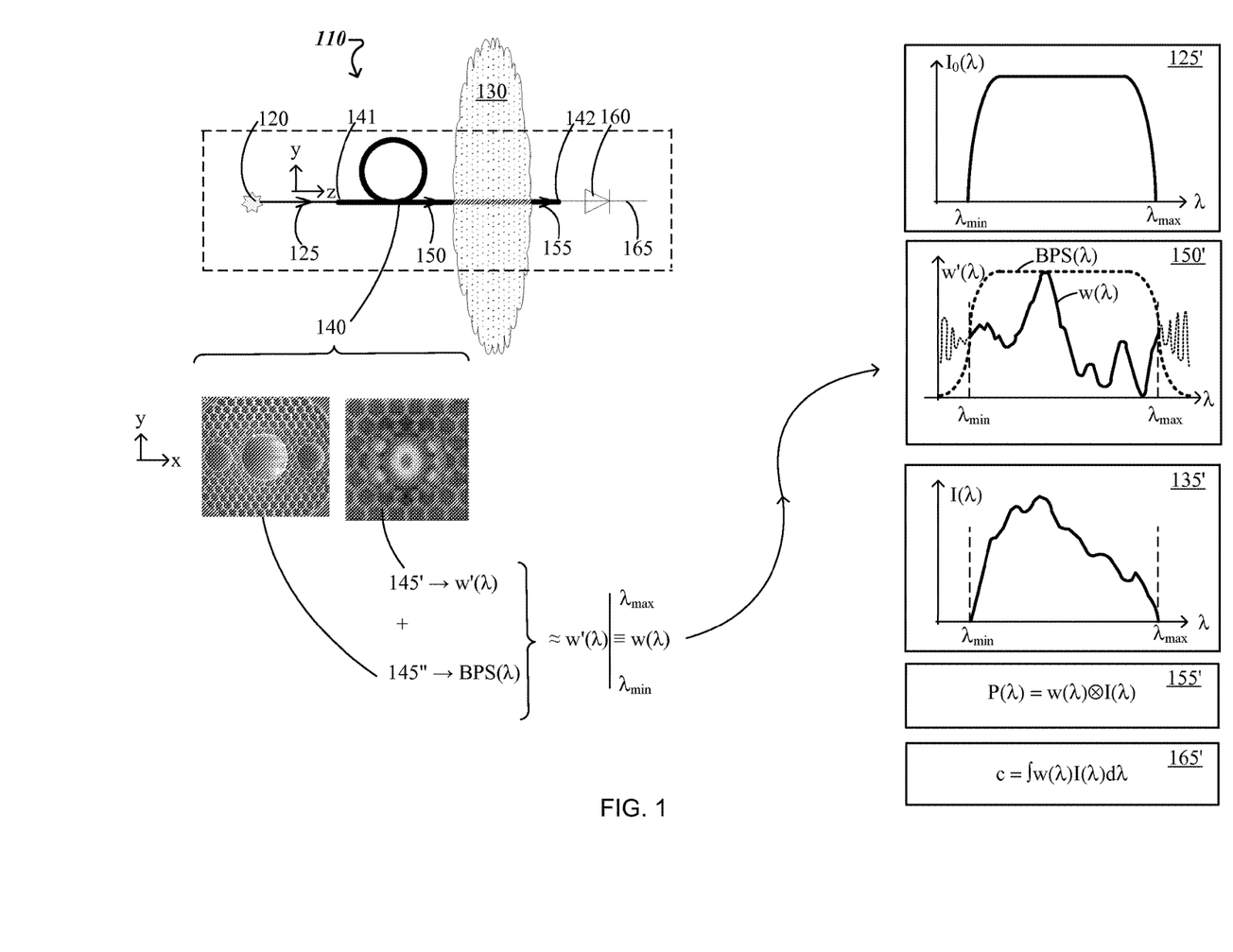
FIG. 1 shows an example of an optical analysis tool for measuring a characteristic of a sample using a band-limited ICE formed from hollow-core fiber.

FIG. 1 shows a schematic of an optical analysis tool 110 for measuring a property of a sample 130 using a band-limited ICE 140 formed from hollow-core fibers. In this example, the optical analysis tool 110 includes a light source 120, the band-limited ICE 140 and an optical transducer 160.

The optical analysis tool 110 is configured to probe the sample 130 (e.g., wellbore gases or liquids, stationary or flowing) to determine an amount (e.g., a value) of a given characteristic (also referred to as a property to be measured) of the probed sample 130. The property to be measured can be any one of multiple properties of the sample 130 including concentration of a given substance in the sample, a gas-oil-ratio (GOR), pH value, density, viscosity, etc.

The light source 120 provides light 125 to the band-limited ICE 140 formed from hollow-core fiber. The light source 120 outputs light 125 with a source spectrum 125' over a particular wavelength range $[\lambda_{min}, \lambda_{max}]$. In some implementations, the source spectrum can have non-zero intensity over the entire or most of the particular wavelength range. In some implementations, the source spectrum extends through UV-vis (0.2-0.8 µm) and near-IR (0.8-2.5 µm) spectral ranges. Alternatively, or additionally, the source spectrum extends through an IR (2.5-100 µm) spectral range. In some implementations, the light source 120 is spectrally tunable and is configured in combination with time resolved signal detection and processing.

Light 125 is provided by the light source 120 at an input end 141 of the band-limited ICE 140. Once inside the constitutive hollow-core fibers of the band-limited ICE 140, light 150 is guided from the input end 141 towards an output end 142 of the band-limited ICE 140. A spectrum of the guided light 150 is equivalent to a spectrum $w(\lambda)$ 150' of the band-limited ICE 140. The spectrum $w(\lambda)$ 150' is a superposition of a spectrum $w'(\lambda)$ corresponding to an ICE core hollow-core fiber and a spectrum $BPS(\lambda)$ corresponding to an optical band-pass filter hollow-core fiber. In the example illustrated in FIG. 1, the ICE core hollow-core fiber has a first hollow-core fiber structure 145', and the optical band-pass filter hollow-core fiber has a second hollow-core fiber structure 145".

In some implementations, the ICE core hollow-core fiber and the optical band-pass filter hollow-core fiber of the band-limited ICE 140 are arranged sequentially from the input end 141 to the output end 142. For example, a first portion of the band-limited ICE 140 beginning at the input end 141 is the optical band-pass filter hollow-core fiber, and a second, remaining portion of the band-limited ICE 140 ending at the output end 142 is the ICE core hollow-core fiber. As another example, the order of the optical band-pass filter hollow-core fiber and the ICE core hollow-core fiber of the band-limited ICE 140 is reversed.

A particular portion of the band-limited ICE 140 formed from hollow-core fiber can be arranged to traverse a sample 130 (e.g., a gas or a liquid), such that the sample fills, over the particular portion, the hollow core of the constitutive hollow-core fibers. For example, a fiber coupler like the one described below in connection with FIGS. 5A-5B can be arranged and configured to couple two portions of a single constitutive hollow-core fiber (or two constitutive hollow-core fibers) and allow the sample 130 to fill the coupler and at least one of the two coupled portions of the fiber(s).

Referring again to FIG. 1, the sample 130 has an optical spectrum $I(\lambda)$ 135' over the wavelength range $[\lambda_{min}, \lambda_{max}]$. Here, the notion that the sample 130 has an optical spectrum $I(\lambda)$ 135' means that a spectrum of light transmitted through (or reflected by) the sample changes in accordance with $I(\lambda)$ 135'. In general, the spectrum $I(\lambda)$ 135' of the sample 130 encodes information about multiple characteristics associated with the sample 130, and more specifically the encoded information relates to current values of the multiple characteristics. The guided light 150 interacts with the sample 130 and is modified thereby. In this manner, light 155 that reaches the output end 142 of the band-limited ICE 140 is sample modified light. A spectrum $P(\lambda)$ 155' of the sample modified light 155 corresponds to the optical spectrum $I(\lambda)$ 135' of the sample 130 weighted by the spectrum $w(\lambda)$ 150' of the band-limited ICE 140.

The sample modified light 155 that reaches the output end 142 of the band-limited ICE 140 is detected by the optical transducer 160. The optical transducer 160 outputs a detector signal 165. A signal value (e.g., a voltage) of the detector signal 165 is a result of an integration of the spectrum 155' of the sample modified light 155 over the wavelength range $[\lambda_{min}, \lambda_{max}]$ and is related to the unknown value "c" 165' of the characteristic to be measured for the sample 130.

In some implementations, the optical analysis tool 110 can include a second band-limited ICE (not shown in FIG. 1) associated with a second optical spectrum $w''(\lambda)$. Here, a second ICE core hollow-core fiber is chosen such that the second optical spectrum $w''(\lambda)$ is associated, over the wavelength range $[\lambda_{min}, \lambda_{max}]$, with a second characteristic of the sample 130. Hence, a second spectrum of sample modified light corresponds to the spectrum $I(\lambda)$ 135' of the sample 130 weighted by the second optical spectrum $w''(\lambda)$ over the wavelength range $[\lambda_{min}, \lambda_{max}]$, such that a second value of a second detector signal is related to a value of the second characteristic for the sample 130.

In some implementations, the value 165' of the characteristic to be measured can be logged along with a measurement time, geo-location, and other metadata, for instance. In some implementations, the detector signal 165, which is related to a characteristic to be measured by the optical analysis tool 110, can be used as a feedback signal to adjust the characteristic of the sample, to modify the sample or environmental conditions associated with the sample, as desired.

The optical spectrum $w(\lambda)$ 150' is determined offline by applying conventional processes to a set of calibration spectra $I(\lambda)$ of the sample which correspond to respective known values of the characteristic to be measured. As illustrated by optical spectrum $w(\lambda)$ 150', optical spectra generally may include multiple local maxima (peaks) and minima (valleys) between $\lambda_{min}$ and $\lambda_{max}$. The peaks and valleys may have the same or different amplitudes. For instance, an optical spectrum w(λ) can be determined through regression analysis of $N_c$ calibration spectra $I_j(\lambda)$ of a sample, where j=1, . . . , $N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum w(λ) 150' through such regression analysis can be $N_c$=10, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum w(λ) 150'. In this manner, when a value of the given characteristic for the sample is unknown, a spectrum $I_u(\lambda)$ of the sample is weighted by the ICE core hollow-core fiber of the band-limited ICE 140 to determine a magnitude of the spectral pattern corresponding to the optical spectrum w(λ) 150' within the spectrum $I_u(\lambda)$. The determined magnitude is proportional to the unknown value of the given characteristic for the sample.

For example, the sample can be a mixture (e.g., the wellbore gas 130) containing substances X, Y and Z, and the characteristic to be measured for the mixture is concentration $c_X$ of substance X in the mixture. In this case, $N_c$ calibration spectra $I_j(\lambda)$ were acquired for $N_c$ samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE core hollow-core fiber, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICE core hollow-core fibers. In this manner, when a new sample of the mixture (e.g., the wellbore gas 130) has an unknown concentration $c_X$ of the X substance, for instance, a spectrum $I_u(\lambda)$ of the new sample is weighted with the first ICE core hollow-core fiber to determine a magnitude of the first spectral pattern within the spectrum $I_u(\lambda)$. The determined magnitude is proportional to the unknown value of the concentration $c_X$ of the X substance for the new sample.

In the example illustrated in FIG. 1, the band-limited ICE 140 of the optical analysis tool 110 is described generally as an ICE core formed from an ICE core hollow-core fiber optically coupled to an optical band-pass filter formed from an optical band-pass filter hollow-core fiber. Examples of hollow-core fibers used as the ICE core of the band-limited ICE 140 in the optical analysis tool 110 are described below.

Figure 2:
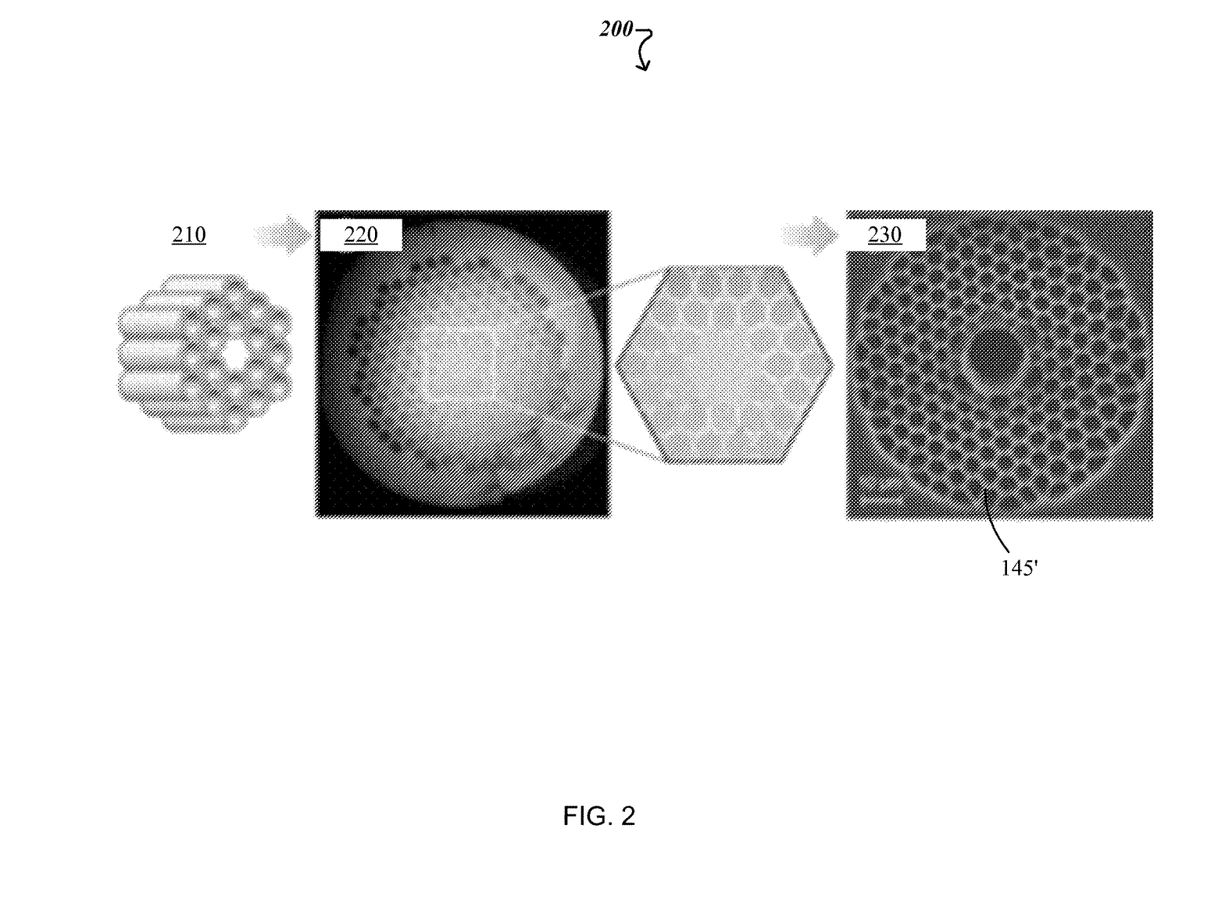
FIG. 2 shows aspects of a hollow-core fiber used as an ICE core and a process of forming the hollow-core fiber.

FIG. 2 shows an example of a fabrication process 200 of a hollow-core fiber. At 210, several hundred fused-silica capillaries are stacked together. At 220, the stack is inserted into a tube. At 230, the stack inserted in the tube is drawn down to fiber. Here, the capillaries fuse together, and their bores become the tiny channels needed in the final fiber with hollow-core fiber structure 145'. In this manner, a channel of the hollow-core fiber structure 145' has walls formed from the constitutive material(s) of the capillaries, e.g., fused silica. Moreover, the walls of the plurality of channels represent vertices of the close-packed array of channels of the hollow-core fiber structure 145'. Because the capillaries used to form the channels have thin walls, the thickness of the walls is about ten times smaller than an inner diameter of the channels. Although the amount of glass contained in the hollow-core fiber structure 145' is small, this glass causes attenuation of light guided by the hollow-core fiber formed through the process 200. Such attenuation may be a limiting feature for fiber optic data communication purposes. However, for purposes of using the hollow-core fiber formed through process 200 as components of a band-limited ICE 140, this is an important feature because the foregoing attenuation may have spectral characteristics that define either an ICE core optical spectrum w(λ) of an optical core or an optical spectrum BPS(λ) of a band-pass filter.

In some implementations of the process 200 for fabricating hollow-core fiber, additional material (in the form of fine fibers) is inserted into the stack at each interstitial point. Ideally, the hollow core fiber would be formed so as to introduce a single core-localized photonic state within a band-gap corresponding to the cladding structure. Light introduced into this state would then be unable to escape from the hollow core fiber through the surrounding cladding material. For example, at 210, a channel of the hollow-core fiber structure 145' can be formed by omitting one or more entire unit cells from the photonic crystal structure of the hollow-core fiber. As another example, a channel that has a larger diameter than diameters of the plurality of channels of hollow-core fiber structure 145' can be formed by inserting an extra, larger tube into the bundle of capillaries to define the larger diameter channel. This tube replaces the several capillaries omitted from the capillary bundle. In this manner, the channels formed from capillaries are prevented from "falling" into the larger diameter channel formed from the larger tube. Moreover, the obtained larger diameter channel has other beneficial effects. In particular, the addition of the extra glass around the larger diameter channel leads to the introduction of additional guided modes into the band-gap, called "surface" modes. These surface modes exist in the same spectral range as the core-guided "air" mode, but have far higher dispersion due to their large overlap with the glass.

Figure 3A:
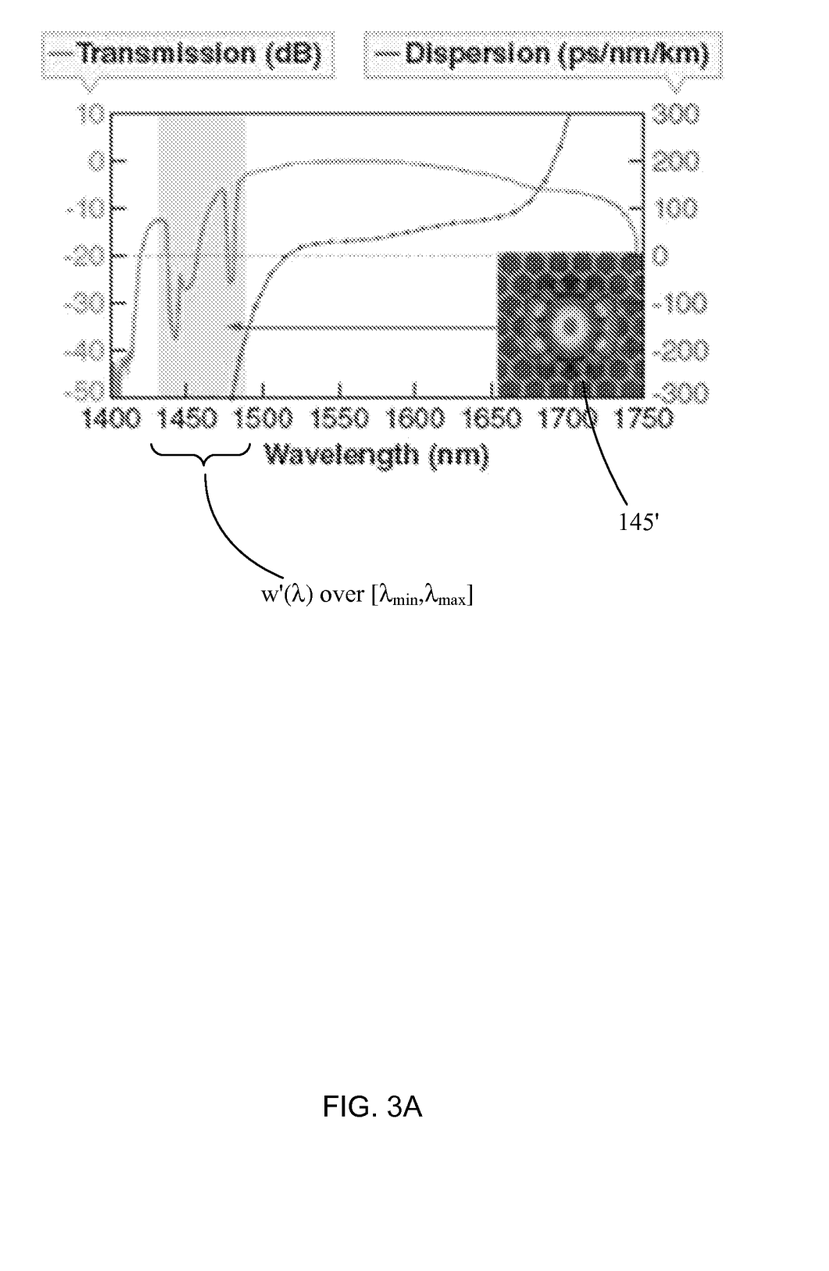
FIGS. 3A-3B show aspects of a hollow-core fibers and corresponding optical spectra of ICE cores formed from the hollow-core fibers.

FIG. 3A shows that, for the hollow-core fiber structure 145' of a hollow-core fiber, interaction of the surface modes with the air mode greatly increases the attenuation and dispersion of the air mode in some wavelength ranges. Such increases in attenuation and dispersion may be undesired for hollow-core fiber communications applications, however, these features are to be exploited for ICE core development. Here, the attenuation of the hollow-core fiber represents, over the operational wavelength range $[\lambda_{min},\lambda_{max}]$, the optical spectrum w'(λ) of the ICE core. As such, the hollow-core fiber structure 145' of the ICE core hollow-core fiber is chosen such that the optical spectrum w'(λ) associated with the ICE core is spectrally equivalent, over the wavelength range $[\lambda_{min},\lambda_{max}]$, to an optical spectrum w(λ) 150' associated with the characteristic to be measured.

For example, a desired optical spectrum w'(λ) associated with an ICE core can be obtained by careful selection of channel wall thickness and channel inner diameter, in combination with a draw ratio during extrusion, as the foregoing engineering parameter combination dictates the final characteristics of the hollow-core fiber structure 145' of the ICE core hollow-core fiber. Also, the refractive index of the glass can be used as an additional engineering parameter for obtaining a desired optical spectrum w'(λ) associated with the ICE core. In this manner, an optical wavelength range of hollow-core fiber based ICE cores can extend into the mid-IR, which is currently a challenge for thin-film interference based ICE cores.

Various other microstructures of hollow-core optical fibers can be used to form an ICE core hollow-core fiber. In other implementations, two or more hollow-core optical fibers with different microstructures can be chained together to obtain a desired optical spectrum w'(λ), as described below.

Figure 3B:
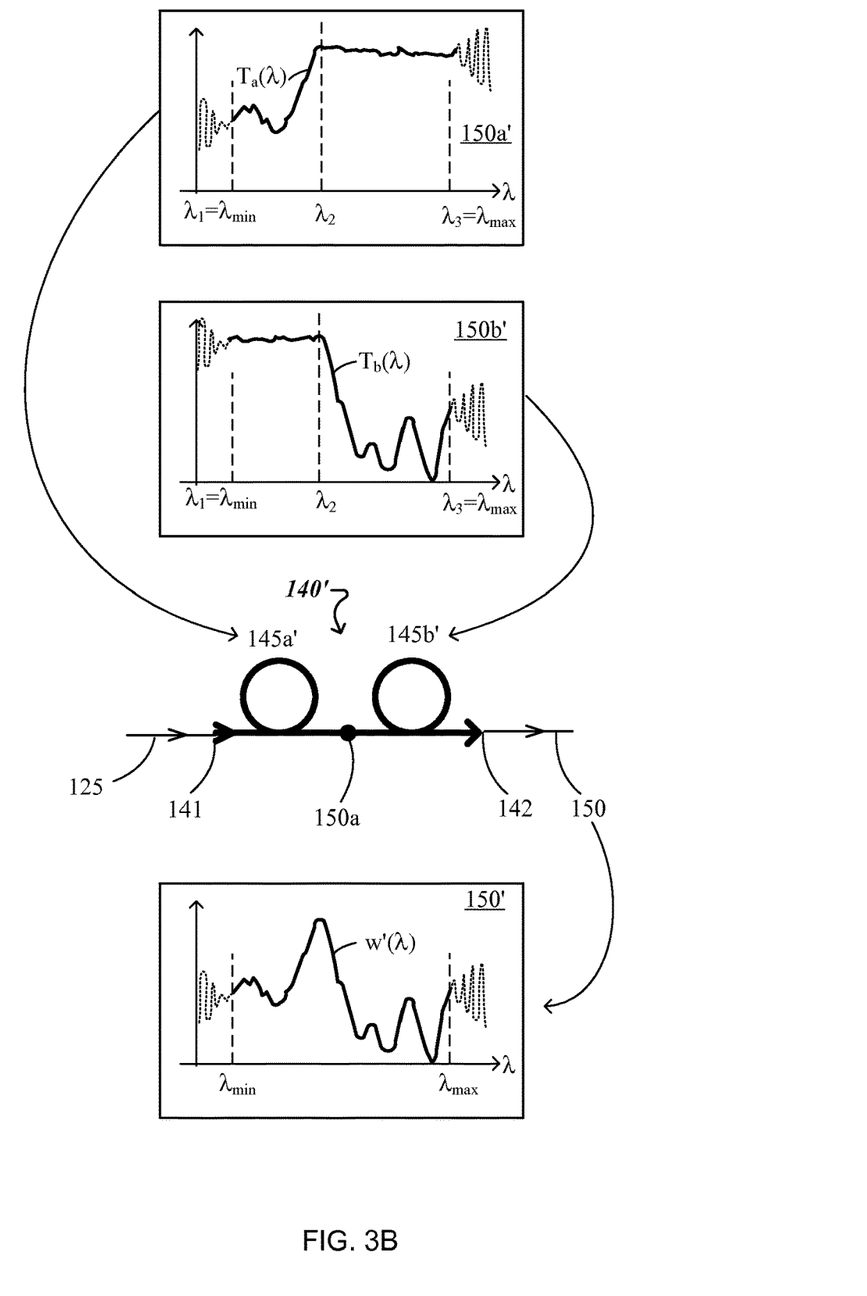

FIG. 3B shows an ICE core 140' that includes a first hollow-core optical fiber having a first hollow-core fiber structure 145a' and a second hollow-core optical fiber having a second hollow-core fiber structure 145b'. The ICE core 140' has an input end 141 which corresponds to an input end of the first hollow-core optical fiber and an output end 142 which corresponds to an output end of the second hollow-core optical fiber. In this example, an output end of the first hollow-core optical fiber is optically coupled with an input end of the second hollow-core optical fiber. Moreover, the first hollow-core fiber structure 145a' of the first hollow-core fiber is chosen such that a first optical transmission spectrum $T_a(\lambda)$ 150a' associated with the first hollow-core fiber is spectrally equivalent, over a first wavelength range $[\lambda_1 = \lambda_{min}, \lambda_2]$, to the optical spectrum w'(λ) 150' associated with the characteristic to be measured. Additionally, the second hollow-core fiber structure 145b' of the second hollow-core fiber is chosen such that a second optical transmission spectrum $T_b(\lambda)$ 150b' associated with the second hollow-core fiber is spectrally equivalent, over a second wavelength range $[\lambda_2, \lambda_3 = \lambda_{max}]$, to the optical spectrum w'(λ) 150' associated with the characteristic to be measured.

In this manner, source light 125 can be received by the ICE core 140' at its input end 141 and guided through the first hollow-core fiber with first hollow-core fiber structure 145a'. At the junction between the first hollow-core fiber and the second hollow-core fiber, the guided light 150a has a spectrum $T_a(\lambda)$ 150a' in accordance with the first hollow-core fiber structure 145a'. Further, the ICE core 140' continues to guide the light 150a through the second hollow-core fiber with second hollow-core fiber structure 145b' and outputs, at the output end 142, output light 150. Here, the output light 150 has a spectrum w'(λ) 150', over the wavelength range $[\lambda_1 = \lambda_{min}, \lambda_3 = \lambda_{max}]$, that is a combination of the first optical transmission spectrum $T_a(\lambda)$ 150a' and the second optical transmission spectrum $T_b(\lambda)$ 150b', in accordance with a combination of the first hollow-core fiber structure 145a' and the second hollow-core fiber structure 145b'.

Moreover, contributions of the optical spectrum w'(λ) associated with a hollow-core fiber structure 145' of an ICE core hollow-core fiber that are from wavelengths outside a wavelength range $[\lambda_{min}, \lambda_{max}]$ are removed from the guided light 150, because of a hollow-core fiber structure 145" of an optical band-pass filter hollow core fiber. In this manner, analysis noise—potentially caused by such "outside-of-band" contributions which may not be spectrally equivalent to the optical spectrum w(λ) 150' associated with the characteristic to be measured—is reduced. Hence, contributions of the optical spectrum I(λ) 135' of the sample that are from wavelengths outside the wavelength range $[\lambda_{min}, \lambda_{max}]$ are weighted to zero. Examples of hollow-core fibers used as the optical band-pass filter of the band-limited ICE 140 in the optical analysis tool 110 are described below.

Figure 4A:
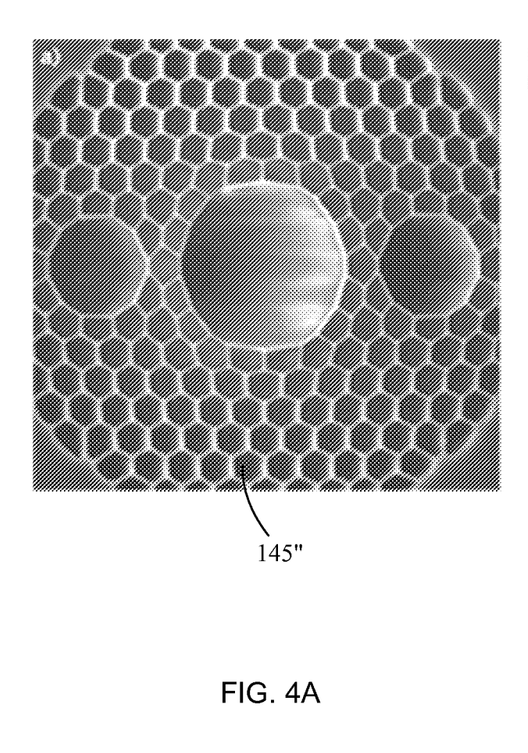
FIGS. 4A-4B show aspects of a hollow-core fiber and band pass spectra of optical band pass filters formed from the hollow-core fiber.
Figure 4B:
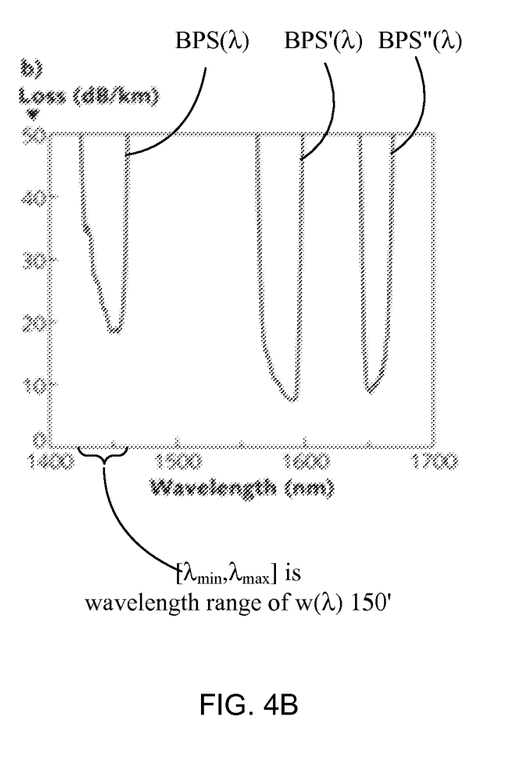

FIG. 4A shows another example of a hollow-core fiber having a honeycomb hollow-core fiber structure 145" with multiple channels. Here, the multiple channels include a central main channel having inner diameter $D_1$, and two smaller side channels or "shunt" channels having inner diameter $D_2 < D_1$. Note, however, that the diameters $D_2$ of the two shunt channels are about three times larger than diameters of most of the channels that form the hollow-core fiber structure 145". The shunt channels allow unwanted modes in the central channel to leak out into the cladding of the hollow-core fiber. FIG. 4B shows transmission of the hollow-core fiber with a central channel and two shunt channels. In the example illustrated in FIGS. 4A-4B, significant loss is present in some regions of the optical spectrum. This is analogous to multiple optical band-pass filters. Conventional optical band-pass filters used to limit the band of ICE cores utilize thin-film interference filters that allow singular optical regions. Multiple band-pass optical regions, e.g., BPS(λ), BPS'(λ), BPS"(λ), are interesting for ICE technology and may allow for previously un-realized ICE designs to be implemented. Hollow-core fiber structures such as hollow-core fiber structure 145" of the optical band-pass filter hollow core fiber illustrated in FIGS. 4A-4B allow use of only one light source emitting light having a broad source spectrum for multiple applications, each application having an associated wavelength range $[\lambda_{min}, \lambda_{max}]$, $[\lambda'_{min}, \lambda'_{max}]$ and $[\lambda''_{min}, \lambda''_{max}]$ overlapped over respective band-pass optical regions BPS(λ), BPS'(λ), BPS"(λ), for instance.

Various other hollow-core optical fibers can be used to form optical band-pass elements with multiple regions of attenuation.

Figures 5A, 5B:
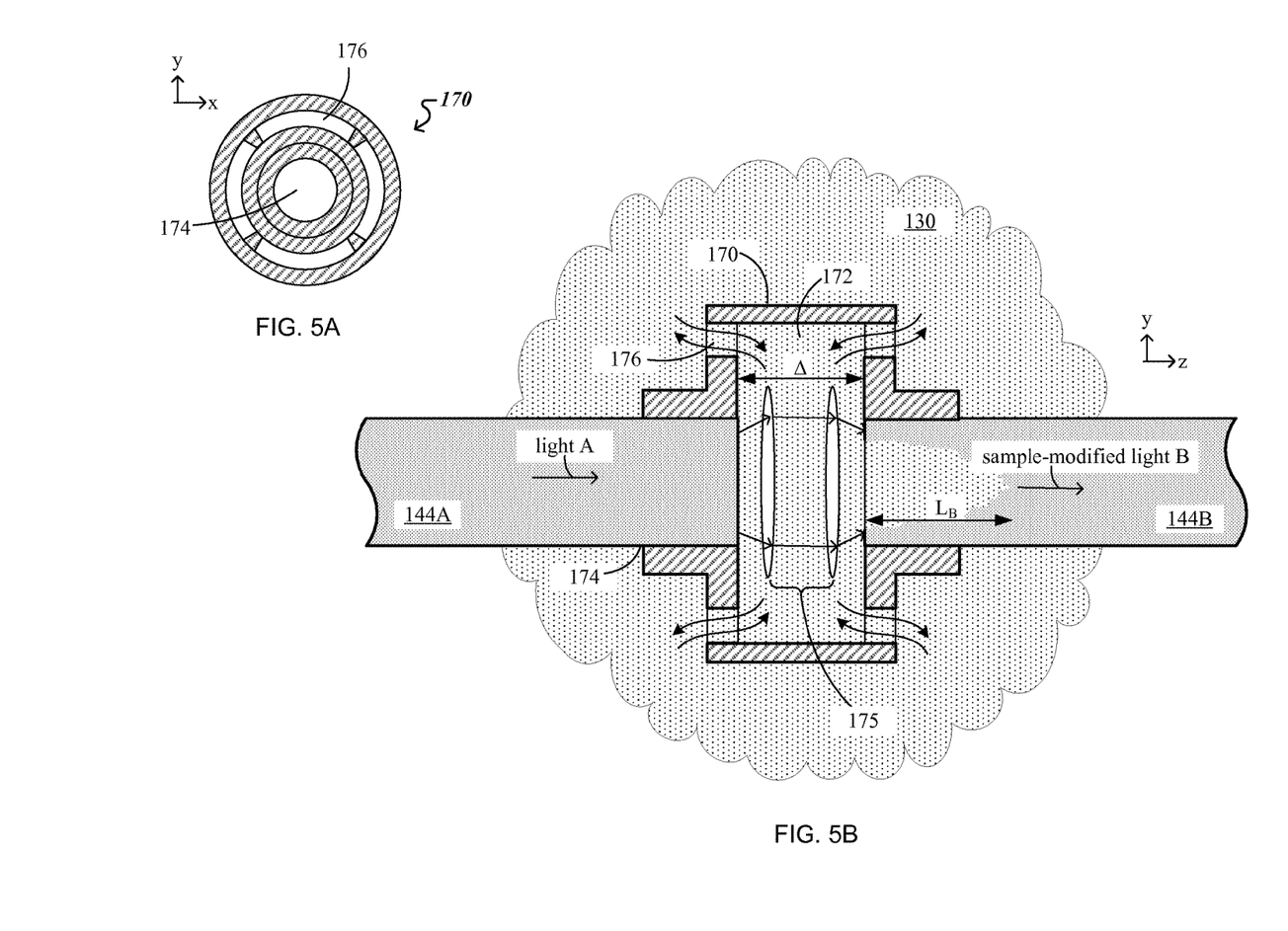
FIGS. 5A-5B show aspects of a fiber coupler configured to allow a fluid sample to partially fill a portion of a hollow-core fiber.

Additionally, hollow-core fiber based ICEs can be engineered to allow samples in the form of a fluid (e.g., gas) to be channeled in the hollow channels of the hollow-core fiber structures 145'/145" to allow for measuring properties of the fluid. FIGS. 5A-5B show aspects of an example of a fiber coupler 170 configured to optically couple a first optical fiber 144A with a second hollow-core optical fiber 144B and to allow a fluid sample 130 to fill, at least, a portion of the hollow-core fiber 144B. In this example, the fiber coupler 170 encloses a coupling chamber 172. The first optical fiber 144A and the second hollow-core optical fiber 144B are inserted in opposing apertures 174 of the fiber coupler 170 such that an output face of the first optical fiber 144A and an input face of the second hollow-core optical fiber 144B are separated by a distance Δ.

Optionally, the fiber coupler 170 can include an optical system 175 disposed in the coupling chamber 172 and formed from one or more lenses configured to capture diverging output light from the first optical fiber 144A and focus it onto the input face of the second hollow-core optical fiber 144B. For instance, for an optical system 175 that includes two lenses, each of thickness of about 0.9 mm, and a lens-to-lens separation of about 2 mm, the output face of the first optical fiber 144A and the input face of the second hollow-core optical fiber 144B can be separated by a distance Δ≤5 mm. When no optical system 175 is present in the coupling chamber 172 of the fiber coupler 170, the distance Δ can be shorter, e.g., Δ≤3, 2 or 1 mm.

Moreover, the fiber coupler 170 has one or more intake/outtake (I/O) apertures 176 through which a fluid sample 130 (e.g., a gas) enters or exits the coupling chamber 172. In this manner, the fluid sample 130 can penetrate, along the z-axis, a hollow-core fiber structure 145B' of the second hollow-core optical fiber 144B at least over a portion thereof. In some cases, a length $L_B$, along the z-axis, of the portion of the second hollow-core optical fiber 144B over which the fluid sample 130 penetrates can be of order $L_B \leq 10$ mm or less. In other cases, the fluid sample 130 penetrates a portion of the second hollow-core optical fiber 144B having a length of $L_B = 1, 10, 20$ m or other lengths.

Light A guided through the first optical fiber 144A has an optical spectrum $w_A'(\lambda)$. If no sample were present in the coupling chamber 172, then light B coupled into and guided by the second hollow-core optical fiber 144B would have a spectrum S(λ) that is the spectrum $w_A'(\lambda)$ of the guided light A weighted by an optical spectrum $w_B(\lambda)$ associated with the hollow-core fiber structure 145B' of the second hollow-core optical fiber 144B, $S(\lambda)=w_B'(\lambda)\otimes w_A'(\lambda)$. Here, the weighting operator $\otimes$ has the following property: $w'(\lambda)\otimes w'(\lambda)=w'(\lambda)$.

However, in the example illustrated in FIG. 5B, the guided light A interacts with the fluid sample 130 inside the coupling chamber 172 and along the length $L_B$ inside the hollow-core fiber structure 145B' of a portion of the second hollow-core optical fiber 144B. Here, the fluid sample 130 has a spectrum $I(\lambda)$. As such, in this example, the sample modified light B is the light guided by the second hollow-core optical fiber 144B once the fluid sample 130 has modified the guided light A (e.g., via the interaction of the guided light A with the fluid sample 130). Here, the sample modified light B has a spectrum $P(\lambda)$ that is the spectrum $w_A'(\lambda)$ of the guided light A weighted by both the optical spectrum $I(\lambda)$ of the fluid sample 130 and the optical spectrum $w_B(\lambda)$ associated with the hollow-core fiber structure 145B' of the second hollow-core optical fiber 144B, $P(\lambda)=w_B'(\lambda)\otimes I(\lambda)\otimes w_A'(\lambda)$.

In some implementations, the first optical fiber 144A can be a first hollow-core optical fiber 144A having the same hollow-core fiber structure 145B' as the second hollow-core optical fiber 144B. In this case, the spectrum of the sample modified light B is $P(\lambda)=w_B'(\lambda)\otimes I(\lambda)\otimes w_B'(\lambda)=I(\lambda)\otimes w_B'(\lambda)$. This case corresponds to implementations in which an ICE core made from a single hollow-core fiber has a first portion 144A and a second portion 144B, where the second portion 144B is connected to the first portion 144A using a coupler 170 to allow for the fluid sample 130 to penetrate inside the hollow-core fiber structure 145B' of the ICE core.

In other implementations, the first optical fiber 144A can be a first hollow-core optical fiber 144A having a hollow-core fiber structure 145A'' corresponding to an optical band-pass spectrum $w_A'(\lambda)=BPS(\lambda)$. In this case, the spectrum of the sample modified light B is $P(\lambda)=w_B'(\lambda)\otimes I(\lambda)\otimes BPS(\lambda)$. This case corresponds to implementations in which an ICE core made from hollow-core fiber is chained between an optical band-pass filter made from hollow-core fiber and a transducer, where a coupler 170 used to couple the ICE core and the optical band-pass filter allows for the fluid sample 130 to penetrate inside the hollow-core fiber structure 145B' of a hollow-core fiber of the ICE core and the hollow-core fiber structure 145A'' of a hollow-core fiber of the optical band-pass filter.

In yet other implementations, the first optical fiber 144A can be a first hollow-core optical fiber 144A having a hollow-core fiber structure 145A'' corresponding to an optical band-pass spectrum $w_A'(\lambda)=BPS(\lambda)$ and the second hollow-core optical fiber 144A also has a hollow-core fiber structure 145A'' corresponding to the same optical band-pass spectrum $w_B'(\lambda)=w_A'(\lambda)=BPS(\lambda)$. In this case, the spectrum of the sample modified light B is $P(\lambda)=BPS(\lambda)\otimes I(\lambda)\otimes BPS(\lambda)=I(\lambda)\otimes BPS(\lambda)$. This case corresponds to implementations in which an optical band-pass filter made from a single hollow-core fiber has a first portion 144A and a second portion 144B, where the second portion 144B is connected to the first portion 144A using a coupler 170 to allow for the fluid sample 130 to penetrate inside the hollow-core fiber structure 145A'' of the optical band-pass filter. In either of the foregoing three implementations, the fluid sample 130 can penetrate, along the z-axis, the hollow-core fiber structure 145B' or 145A'' of the first hollow-core optical fiber 144A at least over a portion thereof. In some cases, a length $L_A$, along the z-axis, of the portion of the first hollow-core optical fiber 144A over which the fluid sample 130 penetrates can be on the same order as $L_B$.

In some other implementations, the first optical fiber 144A can be a supply optical fiber 144A configured to guide light A from a broadband light source (e.g., light source 120 from FIG. 1) that emits light having an emission spectrum that is substantially constant over the wavelength range $[\lambda_{min},\lambda_{max}]$, $I_0(\lambda)=1$, such that a spectrum of the guided light A output by the first optical fiber 144A is substantially unchanged from the emission spectrum, $w_A'(\lambda)\approx I_0(\lambda)=1$. The supply optical fiber 144A can be a conventional multimode optical fiber including solid (as opposed to hollow) core and cladding. In this case, the spectrum of the sample modified light B is $P(\lambda)\approx w_B'(\lambda)\otimes I(\lambda)$. This case corresponds to implementations in which an ICE core made from hollow-core fiber is chained between a supply optical fiber and a transducer, where a coupler 170 used to couple the ICE core and the supply optical fiber allows for the fluid sample 130 to penetrate inside the hollow-core fiber structure 145B' of a hollow-core fiber of the ICE core.

A band-limited ICE that contains a hollow-core fiber based ICE core and one or more hollow-core fiber based optical band-pass filters can be used in the same applications as conventional band-limited ICE. However, analysis tools (e.g., optical analysis tool 110 from FIG. 1) equipped with the disclosed band-limited ICE can be used for applications (e.g., remote sensing) that require access to hostile environments (e.g., downhole or inside/adjacent corrosive systems) which are not easily accessible for analysis tools based on conventional band-limited ICE. As such, the disclosed technologies can enable distributed sensors to be located far away from a light source. In this manner, to monitor the oil content in a pipeline, a light source (e.g., light source 120 from FIG. 1) operating on a rig (above the ground level) may provide light through an optical fiber, such that the light source can be disposed thousands of feet away (e.g., 300-3000 m under the ground level) from a location where a measurement is made (e.g., a location of a fiber coupler 170 from FIG. 5B). As such, the disclosed technologies may eliminate problems associated with locating a light source downhole in downhole applications, hence, simplifying fabrication of downhole optical analysis tools.

For example, a light source, disposed above the ground, is configured to provide source light and can be connected to an input end 141 of a band-limited ICE 140 formed from hollow-core fiber. Here, a first portion (e.g., 144A) and a second portion (e.g., 144B) of a hollow-core fiber of the band-limited ICE are connected together with a fiber coupler 170 at a measurement site, located at a desired depth under the ground level. As described above, the fiber coupler 170 is configured to allow for a fluid sample 130 adjacent the measurement site to penetrate inside a portion of the hollow-core fiber to cause for the light guided in the first portion 144A of the hollow-core fiber to interact with the fluid sample and to become sample modified light that is guided by the second portion 144B of the hollow-core fiber. The sample modified light is collected at an output end 142 of the band-limited ICE and integrated by a transducer (e.g., transducer 160 from FIG. 1) to obtain a signal corresponding to a characteristic of the fluid sample 130.

As another example, a light source, disposed above the ground, can provide source light at a measurement site through a supply optical fiber. The supply optical fiber (e.g., 144A) is connected to an input end 141 of a band-limited ICE 140 formed from hollow-core fiber (e.g., 144B) using a fiber coupler 170 located at the measurement site. As described above, the fiber coupler 170 is configured to allow for a fluid sample 130 adjacent the measurement site to penetrate inside a portion of a hollow-core fiber of the band-limited ICE 140 to cause for the source light guided by the supply optical fiber to interact with the fluid sample and to become sample modified light that is guided by the hollow-core fiber of the band-limited ICE 140. As in the previous example, the sample modified light is collected at the output end 142 of the band-limited ICE and integrated by the transducer (e.g., transducer 160 from FIG. 1) to obtain a signal corresponding to a characteristic of the fluid sample 130.

Figure 6A:
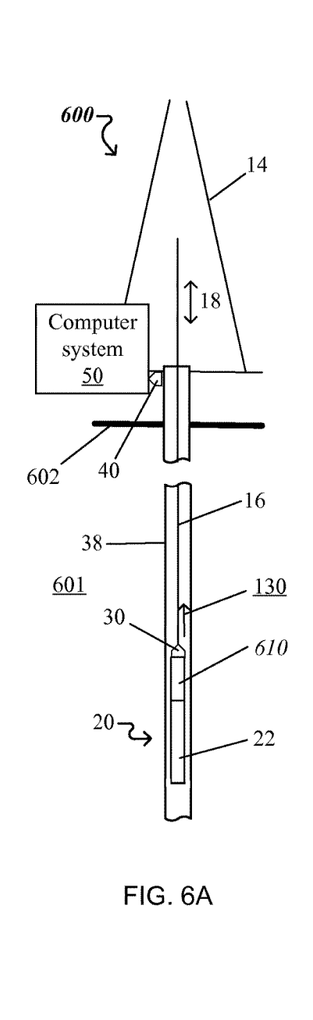
FIGS. 6A-6C show multiple configurations of an example of a system for analyzing wellbore fluids that uses a well logging tool including a band-limited ICE formed from hollow-core fiber.
Figure 6B:
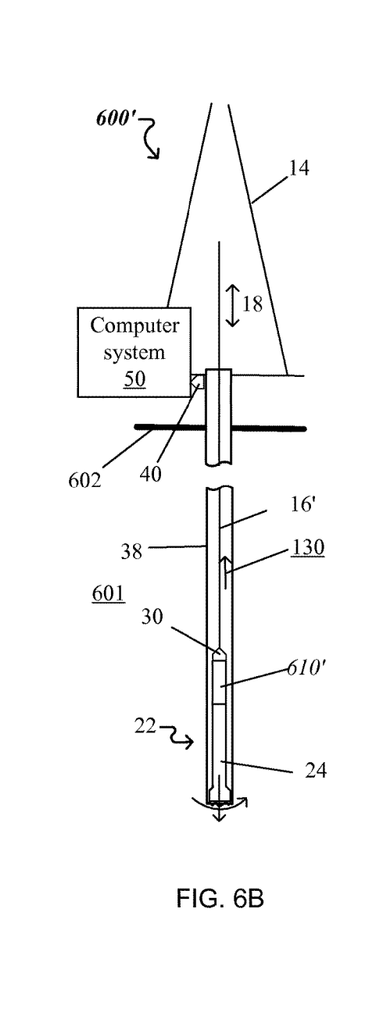
Figure 6C:
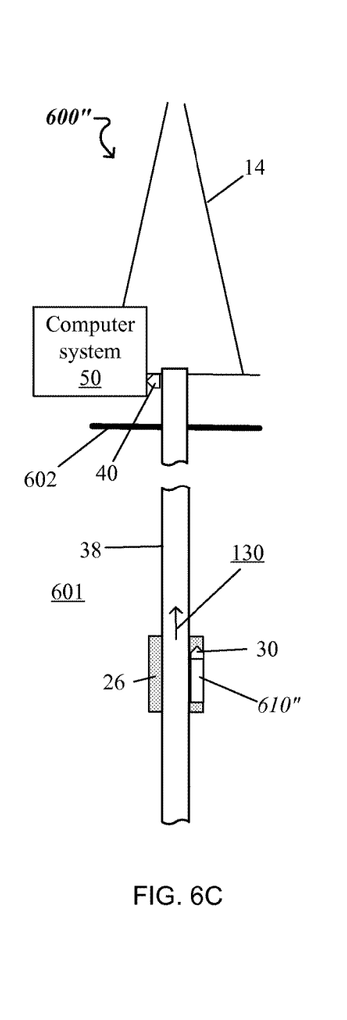

FIGS. 6A-6C show multiple configurations 600, 600', 600" of an example of a system for analyzing wellbore fluids 130 (e.g., gases and liquids), such that analyses are generated from at least some measurements taken with various implementations 610, 610', 610" an optical analysis tool, which includes a band-limited ICE formed from hollow-core fiber, as the one described above in connection with FIG. 1. Here, the optical analysis tool is referred to as a well logging tool, and the disclosed system is referred to as a well logging system.

Each of the configurations 600, 600', 600" of the well logging system illustrated in FIGS. 6A-6C includes a rig 14 above the ground surface 602 and a wellbore 38 below the ground surface. The wellbore 38 extends from the ground surface into the earth 601 and generally passes through multiple geologic formations. In general, the wellbore 38 can contain wellbore fluids 130. The wellbore fluids 130 can be gas, crude petroleum, mud, water or other substances and combinations thereof. Moreover, the wellbore fluids 130 may be at rest, or may flow toward the ground surface 602, for instance. Additionally, surface applications of the well logging tool 610 may include water monitoring and gas and crude transportation and processing.

FIG. 6A shows a configuration 600 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 600 of the well logging system, this information can be generated as a function of a distance (e.g., a depth) with respect to the ground surface 602. In the example illustrated in FIG. 6A, the tool string 20 includes at least a portion of the well logging tool 610, one or more additional well logging tool(s) 22, and a telemetry transmitter 30. Each of the well logging tools 610 and 22 measures one or more characteristics of the wellbore fluids 130. In some implementations, the well logging tool 610 determines values of the one or more characteristics in real time and reports those values instantaneously as they occur in the flowing stream of wellbore fluids 130, sequentially to or simultaneously with other measurement/logging tools 22 of the tool string 20.

FIG. 6B shows another configuration 600' of the well logging system which includes a drilling tool 24 attached to a drill string 16'. The drilling tool 24 includes a drill bit 26, at least a portion of the ICE-based well logging tool 610' configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 602, where the returned drilling mud can be resupplied to the drill string 16' (not shown in FIG. 6B). In this case, the MWD/LWD-configured well logging tool 610' generates and logs information about the wellbore fluids 130 (e.g., drilling mud in this case) adjacent the working drill bit 26.

FIG. 6C shows yet another configuration 600" of the well logging system which includes a permanent installation adjacent to the borehole 38. In some implementations, the permanent installation is a set of casing collars that reinforce the borehole 38. In this case, a casing collar 28 from among the set of casing collars supports at least a portion of the well logging tool 610" and the telemetry transmitter 30. In this manner, the well logging tool 610" determines and logs characteristics of the wellbore fluids 130 adjacent the underground location of the casing collar 28.

In each of the above configurations 600, 600' and 600" of the well logging system, the values of the one or more characteristics measured by the well logging tool 610, 610', 610" are provided (e.g., as a detector signal 165) to the telemetry transmitter 30. The latter communicates the measured values to a telemetry receiver 40 located above the ground surface 602. The telemetry transmitter 30 and the telemetry receiver 40 can communicate through a wired or wireless telemetry channel. In some implementations of the system configurations 600, 600' illustrated in FIGS. 6A and 6B, e.g., in slickline or coiled tubing applications, measurement data generated by the well logging tool 110 can be written locally to memory of the well logging tool 610, 610', 610".

The measured values of the one or more characteristics of the wellbore fluids 130 received by the telemetry receiver 40 can be logged and analyzed by a computer system 50 associated with the rig 14. In this manner, the measurement values provided by the well logging tool 610, 610', 610" can be used to generate physical and chemical information about the wellbore fluids 130 in the wellbore 38.

Characteristics of the wellbore fluids 130 that can be related to the spectrum 135' through the optical spectra associated with the ICE core hollow-core fiber and other ICE core hollow-core fibers (not shown in FIG. 1) of the band-limited ICE 140 are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

In general, innovative aspects of the technologies described herein can be implemented in optical analysis tools that include one or more of the following aspects:

In general aspect 1, an optical analysis tool for analyzing a sample comprises an integrated computational element (ICE), the ICE comprising a first hollow-core fiber, the first hollow-core fiber having a first hollow-core fiber structure configured such that a spectrum of light guided by the first hollow-core fiber is related, over a wavelength range, to a characteristic of the sample.

In aspect 2 according to aspect 1, the ICE further comprises a second hollow-core fiber optically coupled to the first hollow-core fiber, the second hollow-core fiber having a second hollow-core fiber structure different from the first hollow-core fiber structure, the second hollow-core fiber structure configured such that the second hollow-core fiber blocks light guided there through at wavelengths that are either shorter than the wavelength range or longer than the wavelength range, or both shorter and longer than the wavelength range.

In aspect 3 according to aspect 2, the second hollow-core fiber structure of the second hollow-core fiber is formed such that a spectrum of the light guided through the second hollow-core fiber includes two or more optical band-pass filter spectra, at least one of the optical band-pass filter spectra overlapping the wavelength range over which the light guided by the first hollow-core fiber is related to the characteristic of the sample.

In aspect 4 according to aspect 3, the ICE is a band-limited ICE, the first hollow-core fiber is an ICE core of the band-limited ICE, and the second hollow-core fiber is an optical band-pass filter of the band-limited ICE.

In aspect 5 according to aspect 4, the band-limited ICE further comprises a second ICE core, the second ICE core comprising a third hollow-core fiber, the third hollow-core fiber having a third hollow-core fiber structure configured such that a spectrum of light guided by the third hollow-core fiber is related, over a second wavelength range, to a second characteristic of the sample. Here, the light guided through the second hollow-core fiber includes a first optical band-pass filter spectrum corresponding to the wavelength range over which the light guided by the first hollow-core fiber is related to the characteristic of the sample, and a second optical band-pass filter spectrum corresponding to the second wavelength range over which the light guided by the third hollow-core fiber is related to the second characteristic of the sample.

In aspect 6 according to aspect 1 or aspect 2, the optical analysis tool further comprises a light source coupled with an input end of the ICE, the light source to provide light having a first spectrum over the wavelength range. Here, the first hollow-core fiber of the ICE guides the light provided by the light source at the input end towards an output end of the ICE. Further, the ICE interacts with the sample over a portion of the ICE located between the input and output ends of the ICE, such that the guided light is modified by the sample. Furthermore, a spectrum of the sample-modified light, when integrated over the wavelength range, is related to a value of the characteristic of the sample.

In aspect 7 according to aspect 6, the optical analysis tool further comprises an optical transducer positioned to receive the sample modified light at the output end of the ICE and configured to integrate intensity of the sample modified light across the wavelength range, and produce a signal having a signal value related to the integrated intensity of the sampled modified light, wherein the signal value corresponds to the value of the characteristic of the sample.

In aspect 8 according to aspect 6, the light source is coupled with the input end of the ICE through a supply optical fiber having a length within a predetermined length range.

In aspect 9 according to aspect 8, the predetermined length range of the supply optical fiber is 300-3000 m.

In aspect 10 according to aspect 6, interaction of the ICE with the sample comprises channeling of the sample inside the first hollow-core fiber structure of the first hollow-core fiber of the ICE core, or inside the second hollow-core fiber structure of the second hollow-core fiber of the optical band-pass filter, or inside both.

In aspect 11 according to aspect 6, the optical analysis tool further comprises a fiber coupler configured to couple a first portion of the first hollow-core fiber and a second portion of the first hollow-core fiber. In this aspect, the fiber coupler encloses a coupling chamber in which an output end of the first portion of the first hollow-core fiber and an input end of the second portion of the first hollow-core fiber are spaced apart, and the fiber coupler has one or more intake/outtake apertures configured to allow a fluid sample to enter and exit the coupling chamber, such that once inside the coupling chamber, the fluid sample can penetrate inside the first hollow-core fiber structure of the first portion of the first hollow-core fiber through the output end and inside the first hollow-core fiber structure of the second portion of the first hollow-core fiber through the input end.

In aspect 12 according to aspect 6, the optical analysis tool further comprises a fiber coupler configured to couple the first hollow-core fiber and the second hollow-core fiber. In this aspect, the fiber coupler has one or more intake/outtake apertures configured to allow a fluid sample to enter and exit the coupling chamber, such that once inside the coupling chamber, the fluid sample can penetrate inside the first hollow-core fiber structure of the first hollow-core fiber through the input end and inside the second hollow-core fiber structure of the second hollow-core fiber through the output end.

In aspect 13 according to aspect 6, the optical analysis tool further comprises a fiber coupler configured to couple a first portion of the second hollow-core fiber and a second portion of the second hollow-core fiber. In this aspect, the fiber coupler encloses a coupling chamber in which an output end of the first portion of the second hollow-core fiber and an input end of the second portion of the second hollow-core fiber are spaced apart, and the fiber coupler has one or more intake/outtake apertures configured to allow a fluid sample to enter and exit the coupling chamber, such that once inside the coupling chamber, the fluid sample can penetrate inside the second hollow-core fiber structure of the first portion of the second hollow-core fiber through the output end and inside the second hollow-core fiber structure of the second portion of the second hollow-core fiber through the input end.

In aspect 14 according to aspect 6, the optical analysis tool further comprises a fiber coupler configured to couple the first hollow-core fiber and a supply optical fiber. In this aspect, the fiber coupler encloses a coupling chamber in which an output end of the supply optical fiber and an input end of the first hollow-core fiber are spaced apart, and the fiber coupler has one or more intake/outtake apertures configured to allow a fluid sample to enter and exit the coupling chamber, such that once inside the coupling chamber, the fluid sample can penetrate inside the first hollow-core fiber structure of the first hollow-core fiber through the input end.

In aspect 15 according to aspect 1 or aspect 2, the wavelength range comprises wavelengths in a range from about 0.2 μm to about 25 μm.

In aspect 16 according to aspect 15, the wavelength range comprises wavelengths in a range from about 0.2 μm to about 2.5 μm.

In aspect 17 according to aspect 15, the wavelength range comprises wavelengths in a range from about 2.5 μm to about 25 μm.

In aspect 18, a well logging system comprises the optical analysis tool of aspect 1 or aspect 2, wherein the sample comprises wellbore gases or liquids and the characteristic of the sample is a characteristic of the wellbore gases or liquids.

In aspect 19 according to aspect 18, the characteristic of the sample is selected from the group consisting of a concentration of a substance in the sample, a pH of the sample, a ratio of concentrations of two different substances in the sample, a phase of the sample, a density of the sample, and a viscosity of the sample.

In aspect 20, a method comprises placing at least a portion of the optical analysis tool of aspect 1 or aspect 2 in a wellbore; and determining the value of a characteristic of a sample in the wellbore using the optical analysis tool of aspect 1 or aspect 2.

In aspect 21 according to aspect 1, the first hollow-core fiber structure comprises a plurality of first channels extending along a longitudinal axis of the first hollow-core fiber, and a second channel centered on the longitudinal axis, where the first channels are disposed around the second channel, and a second inner diameter of the second channel is larger, by a predetermined factor, than a first inner diameter of each of the first capillaries.

In aspect 22 according to aspect 21, the first inner diameter of each of the first channels is less than 5 µm and the predetermined factor is between 3 and 10.

In aspect 23 according to aspect 2, the second hollow-core fiber structure comprises a plurality of third channels extending along a longitudinal axis of the second hollow-core fiber, a central channel centered on the longitudinal axis of the second tube, and two or more shunt channels extending along the central channel and disposed at a particular radial distance from the central channel, where the third channels are disposed around the central channel and the shunt channels, and an inner diameter of each of the shunt channels is smaller than an inner diameter of the central channel and larger than an inner diameter of each of the third channels.

In aspect 24 according to aspect 23, respective centers of the central channel and of the shunt channels are disposed along a common diameter of the second hollow-core fiber structure.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. An optical analysis tool for analyzing a sample, the optical analysis tool comprising:
an integrated computational element (ICE) comprising a first hollow-core fiber and a second hollow-core fiber optically coupled to the first hollow-core fiber, wherein:
the first hollow-core fiber having a first hollow-core fiber structure configured such that a spectrum of light guided by the first hollow-core fiber is related, over a wavelength range, to a characteristic of the sample, and
the second hollow-core fiber having a second hollow-core fiber structure different from the first hollow-core fiber structure configured such that the second hollow-core fiber blocks light guided there through at wavelengths that are either shorter than the wavelength range or longer than the wavelength range, or both shorter and longer than the wavelength range.

2. The optical analysis tool of claim 1, wherein the second hollow-core fiber structure of the second hollow-core fiber is formed such that a spectrum of the light guided through the second hollow-core fiber includes two or more optical band-pass filter spectra, at least one of the optical band-pass filter spectra overlapping the wavelength range over which the light guided by the first hollow-core fiber is related to the characteristic of the sample.

3. The optical analysis tool of claim 2, wherein
the ICE is a band-limited ICE,
the first hollow-core fiber is an ICE core of the band-limited ICE, and
the second hollow-core fiber is an optical band-pass filter of the band-limited ICE.

4. The optical analysis tool of claim 3, wherein
the band-limited ICE further comprises a second ICE core, the second ICE core comprising a third hollow-core fiber, the third hollow-core fiber having a third hollow-core fiber structure configured such that a spectrum of light guided by the third hollow-core fiber is related, over a second wavelength range, to a second characteristic of the sample, and
the light guided through the second hollow-core fiber includes
a first optical band-pass filter spectrum corresponding to the wavelength range over which the light guided by the first hollow-core fiber is related to the characteristic of the sample, and
a second optical band-pass filter spectrum corresponding to the second wavelength range over which the light guided by the third hollow-core fiber is related to the second characteristic of the sample.

5. The optical analysis tool of claim 1, further comprising:
a light source coupled with an input end of the ICE, the light source to provide light having a first spectrum over the wavelength range,
wherein the first hollow-core fiber of the ICE guides the light provided by the light source at the input end towards an output end of the ICE,
wherein the ICE interacts with the sample over a portion of the ICE located between the input and output ends of the ICE, such that the guided light is modified by the sample, and
wherein a spectrum of the sample-modified light, when integrated over the wavelength range, is related to a value of the characteristic of the sample.

6. The optical analysis tool of claim 5, further comprising:
an optical transducer positioned to receive the sample modified light at the output end of the ICE and configured to
integrate intensity of the sample modified light across the wavelength range, and produce a signal having a signal value related to the integrated intensity of the sampled modified light, wherein the signal value corresponds to the value of the characteristic of the sample.

7. The optical analysis tool of claim 5, wherein the light source is coupled with the input end of the ICE through a supply optical fiber having a length within a predetermined length range.

8. The optical analysis tool of claim 7, wherein the predetermined length range of the supply optical fiber is 300-3000 m.

9. The optical analysis tool of claim 5, wherein interaction of the ICE with the sample comprises channeling of the sample inside the first hollow-core fiber structure of the first hollow-core fiber of the ICE core, or inside the second hollow-core fiber structure of the second hollow-core fiber of the optical band-pass filter, or inside both.

10. The optical analysis tool of claim 5 further comprises
a fiber coupler configured to couple a first portion of the first hollow-core fiber and a second portion of the first hollow-core fiber,
wherein the fiber coupler encloses a coupling chamber in which an output end of the first portion of the first hollow-core fiber and an input end of the second portion of the first hollow-core fiber are spaced apart, and
wherein the fiber coupler has one or more intake/outtake apertures configured to allow a fluid sample to enter and exit the coupling chamber, such that once inside the coupling chamber, the fluid sample can penetrate inside the first hollow-core fiber structure of the first portion of the first hollow-core fiber through the output end and inside the first hollow-core fiber structure of the second portion of the first hollow-core fiber through the input end.

11. The optical analysis tool of claim 5 further comprises
a fiber coupler configured to couple the first hollow-core fiber and the second hollow-core fiber,
wherein the fiber coupler encloses a coupling chamber in which an output end of the second hollow-core fiber and an input end of the first hollow-core fiber are spaced apart, and
wherein the fiber coupler has one or more intake/outtake apertures configured to allow a fluid sample to enter and exit the coupling chamber, such that once inside the coupling chamber, the fluid sample can penetrate inside the first hollow-core fiber structure of the first hollow-core fiber through the input end and inside the second hollow-core fiber structure of the second hollow-core fiber through the output end.

12. The optical analysis tool of claim 5 further comprises
a fiber coupler configured to couple a first portion of the second hollow-core fiber and a second portion of the second hollow-core fiber,
wherein the fiber coupler encloses a coupling chamber in which an output end of the first portion of the second hollow-core fiber and an input end of the second portion of the second hollow-core fiber are spaced apart, and
wherein the fiber coupler has one or more intake/outtake apertures configured to allow a fluid sample to enter and exit the coupling chamber, such that once inside the coupling chamber, the fluid sample can penetrate inside the second hollow-core fiber structure of the first portion of the second hollow-core fiber through the output end and inside the second hollow-core fiber structure of the second portion of the second hollow-core fiber through the input end.

13. The optical analysis tool of claim 5 further comprises
a fiber coupler configured to couple the first hollow-core fiber and a supply optical fiber, wherein the fiber coupler encloses a coupling chamber in which an output end of the supply optical fiber and an input end of the first hollow-core fiber are spaced apart, and
wherein the fiber coupler has one or more intake/outtake apertures configured to allow a fluid sample to enter and exit the coupling chamber, such that once inside the coupling chamber, the fluid sample can penetrate inside the first hollow-core fiber structure of the first hollow-core fiber through the input end.

14. The optical analysis tool of claim 1, wherein the wavelength range comprises wavelengths in a range from about 0.2 µm to about 25 µm.

15. The optical analysis tool of claim 14, wherein the wavelength range comprises wavelengths in a range from about 0.2 µm to about 2.5 µm.

16. The optical analysis tool of claim 14, wherein the wavelength range comprises wavelengths in a range from about 2.5 µm to about 25 µm.

17. A well logging system comprising the optical analysis tool of claim 1, wherein the sample comprises wellbore gases or liquids and the characteristic of the sample is a characteristic of the wellbore gases or liquids.

18. The well logging system of claim 17, wherein the characteristic of the sample is selected from the group consisting of a concentration of a substance in the sample, a pH of the sample, a density of the sample, and a viscosity of the sample.

19. A method, comprising:
placing at least a portion of the optical analysis tool of claim 1 in a wellbore; and
determining the value of a characteristic of a sample in the wellbore using the optical analysis tool of claim 1.

20. The optical analysis tool of claim 1, wherein the first hollow-core fiber structure comprises
a plurality of first channels extending along a longitudinal axis of the first hollow-core fiber, and
a second channel centered on the longitudinal axis, where the first channels are disposed around the second channel, and a second inner diameter of the second channel is larger, by a predetermined factor, than a first inner diameter of each of the first capillaries.

21. The optical analysis tool of claim 20, wherein the first inner diameter of each of the first channels is less than 5 um and the predetermined factor is between 3 and 10.

22. The optical analysis tool of claim 1, wherein the second hollow-core fiber structure comprises
a plurality of third channels extending along a longitudinal axis of the second hollow-core fiber,
a central channel centered on the longitudinal axis of the second tube, and
two or more shunt channels extending along the central channel and disposed at a particular radial distance from the central channel, where the third channels are disposed around the central channel and the shunt channels, and an inner diameter of each of the shunt channels is smaller than an inner diameter of the central channel and larger than an inner diameter of each of the third channels.

23. The optical analysis tool of claim 22, wherein respective centers of the central channel and of the shunt channels are disposed along a common diameter of the second hollow-core fiber structure.

\* \* \* \* \*